United States Patent [19]

Finsterwald et al.

[11] Patent Number: 4,802,458
[45] Date of Patent: Feb. 7, 1989

[54] DUAL FUNCTION ULTRASONIC TRANSDUCER PROBES

[75] Inventors: Phillip M. Finsterwald, West Haven, Conn.; Charles W. Howlett, Bailey, Colo.; James W. Ring, Southbury, Conn.

[73] Assignee: Ethicon, Inc., Somerville, N.J.

[21] Appl. No.: 588,021

[22] Filed: Mar. 9, 1984

[51] Int. Cl.⁴ .............................................. A61B 10/00
[52] U.S. Cl. .................................. 128/661.08; 73/634
[58] Field of Search .................... 277/200; 464/19, 79, 464/80, 175; 128/660, 661, 4, 6, 663; 73/621, 629, 633, 634

[56] References Cited

U.S. PATENT DOCUMENTS

| | | | |
|---|---|---|---|
| 326,941 | 9/1885 | Browne | 464/175 |
| 2,882,503 | 4/1959 | Huff et al. | 464/79 |
| 3,403,671 | 10/1968 | Flaherty et al. | 73/621 |
| 3,854,471 | 12/1974 | Wild | 128/660 |
| 4,034,744 | 7/1977 | Goldberg | 128/660 |
| 4,059,098 | 11/1977 | Murdock | 128/660 |
| 4,084,409 | 4/1978 | Wolf et al. | 464/79 |
| 4,121,843 | 10/1978 | Halling | 277/200 |
| 4,149,419 | 4/1979 | Connell, Jr. et al. | 128/660 |
| 4,374,525 | 2/1983 | Baba | 128/4 |
| 4,378,945 | 4/1983 | Trautman | 277/200 |
| 4,407,293 | 10/1983 | Suarez, Jr. et al. | 128/660 |
| 4,466,444 | 8/1984 | Baba | 128/660 |
| 4,476,874 | 10/1984 | Taenzer et al. | 128/663 |
| 4,492,120 | 1/1985 | Lewis et al. | 128/663 |

FOREIGN PATENT DOCUMENTS 0039045 11/1981 European Pat. Off. .

Primary Examiner—Ruth S. Smith

[57] ABSTRACT

An ultrasonic transducer probe is provided which exhibits an angular design, having a body section containing a drive motor and a transducer section. The axes of the two sections are oriented obliquely with respect to each other such that the motor section may be grasped in the manner of a writing instrument while the transducer section is pressed against a patient. In a preferred embodiment, the two sections are coupled together by a flexible bellows and two crystals are mounted on a shaft in the transducer section, one for sector scan imaging and the other for Doppler flow measurement.

5 Claims, 3 Drawing Sheets

DUAL FUNCTION ULTRASONIC TRANSDUCER PROBES

This invention relates to ultrasonic transducer probes and, in particular, to dual function ultrasonic transducer probes configured to perform both diagnostic imaging and flow measurement.

Ultrasonic transducer probes comprise assemblies which hold the ultrasonic transmitting and receiving crystals for ultrasonic diagnostic systems. Transducer probes are manipulated by the doctor or clinician to direct ultrasound into and receive echoes back from a patient's body. The transducer probe may be connected to an articulated arm, or may be hand-held. In either case, the transducer probe is electrically connected, generally by a cable, to the electronic apparatus which activates the transducer crystal and processes and displays the received echo information.

It is desirable for hand-held transducer probes to possess attributes which make them easy and convenient to use. The probe should be lightweight so that it is easy to manipulate without tiring the user. The probe should provide a comfortable grip which allows precise control over the probe location. The grip should also locate the body of the probe and the cable out of the user's way, so that the user can clearly see the position of the transducer crystal on the patient's body.

When the transducer probe is used for Doppler flow measurement it is desirable for it to also possess imaging capability. The dual function probe thereby permits the user to view the tissue structure or vessel in which the flow measurement is being made. The user can then steer a cursor or other indicator in the image to the precise point of flow measurement. Moreover, it is desirable for the Doppler signal beam path to be centered in the image, to allow a clear view of the point at which the flow measurement is being made and the surrounding tissue. A uniformly centered Doppler beam path with respect to the imaged area is to be preferred over arrangements in which the Doppler beam path angularly intersects the image plane, since the latter technique centers the Doppler path only over a small portion of the path, and at times toward the edge of the image. Furthermore, it is desirable to use separate, dedicated transducer crystals for the imaging and flow measurement functions for better resolution and the ability to perform continuous wave Doppler measurements.

A further desirable feature for a flow measurement probe is a small terminus at which the transducer crystal is located. Preferably, the terminus containing the acoustic window of the probe should be only slightly larger than the dimensions of the transducer crystal. This feature is significant when peripheral vascular flow measurements are being performed, such as blood flow measurements in the carotid artery. When making such measurements, it is often necessary to image and measure the flow rate in the artery high along the neck and just under the jawbone. A probe with a small transducer terminus makes it possible to position the transducer against the neck and beneath the mandible, and is thus a more versatile probe for peripheral vascular applications.

In accordance with the principles of the present invention, an ultrasonic transducer probe is provided which is convenient to use and exhibits a relatively small transducer terminus. The transducer probe includes a body section and a transducer section. The axes of the two sections are positioned obliquely with respect to each other, which permits the body to be gripped in the familiar fashion of a writing instrument when the transducer terminus is in smooth contact with the skin of the patient. This angular design allows the transducer probe to be held with the body section and cable located generally above the user's hand and arm, thereby providing an unobstructed view of the location of the transducer section on the patient. The transducer section is only slightly larger than the transducer crystal, which together with the angular design, allows carotid artery imaging and flow measurement high along the neck under the mandible.

In accordance with a further aspect of the present invention, the transducer probe is provided with a sector scanning capability by oscillating the transducer crystal. The transducer crystal is mounted on a first shaft in the transducer section of the probe, and drive means and a second shaft are located in the body section. The two shafts are oriented at an oblique angle, and are connected by a torsionally resistant connecting means so that the drive means will oscillate the second shaft, connecting means, and first shaft and crystal without significant backlash. In a preferred embodiment of the present invention, the connecting means comprises a spring-like bellows device.

In accordance with yet another aspect of the present invention, an imaging transducer crystal and a Doppler transducer crystal are mounted on the first shaft normal to different radii of the first shaft. In an imaging mode of operation, the face of the imaging crystal is oriented toward the acoustic window of the probe and the first shaft is oscillated to provide a sector scan. In the flow measurement mode, the first shaft is turned so that the face of the Doppler crystal is directed toward the acoustic window. The Doppler beam will then be directed through the center or a selected off-center angle of the imaged sector. Alternation between the two modes may be done automatically to update the sector image and freeze a current image while Doppler flow measurements are being performed.

Figure 1:
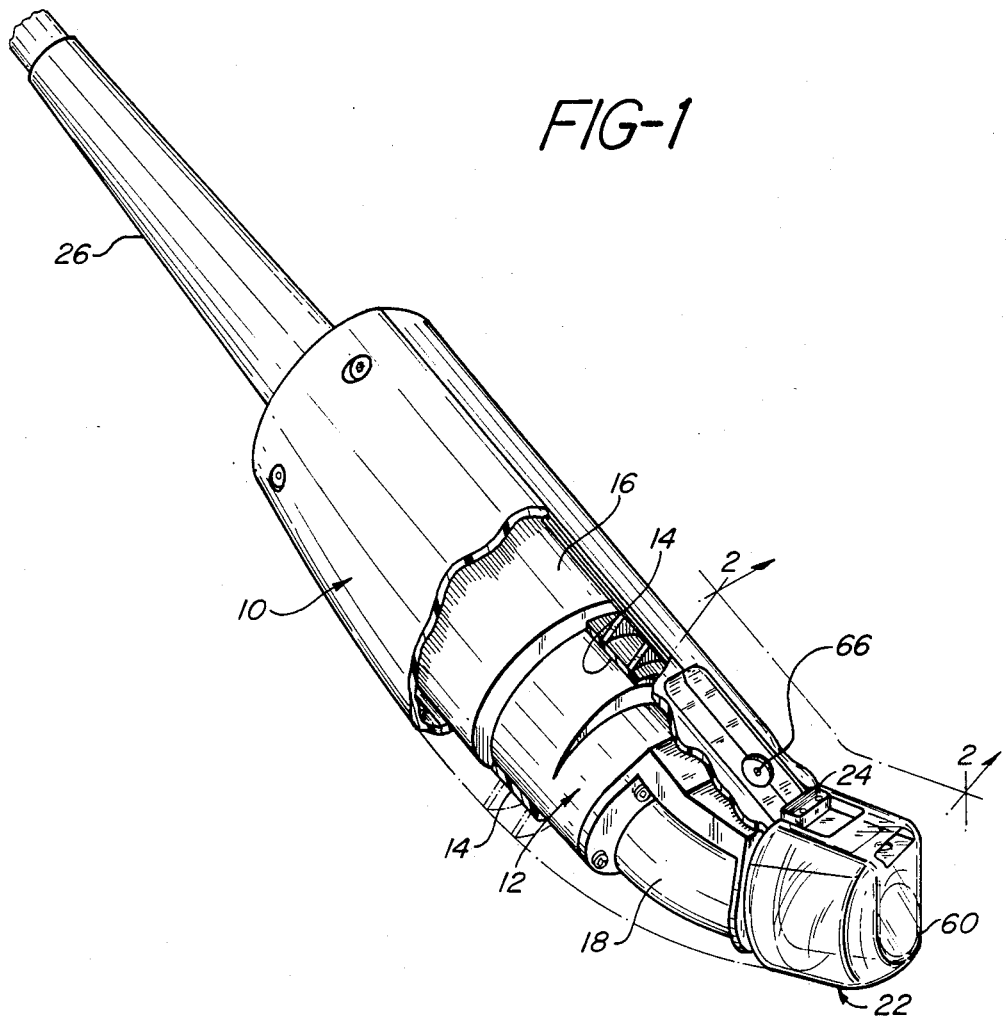
FIG. 1 illustrates a perspective view of an ultrasonic transducer probe constructed in accordance with the principles of the present invention.

Referring to FIG. 1, an ultrasonic transducer probe of the present invention is shown with its plastic case 10 partially broken away to reveal its component elements. Inside the case is a brushless DC motor 12, mounted by a motor housing gasket 14. The motor turns a shaft which is not shown in this FIGURE, which extends from both ends of the motor housing. One end of the motor shaft is connected to a shaft encoder 16, which develops electrical signals indicative of the angular position of the motor shaft. These signals are supplied to a display system (not shown) by way of a cable and motor power cord 26, where they are used to produce a coordinated image of tissue in combination with pulse-echo signals provided by the probe transducers, and also used to control the motor through a servo system.

The other end of the motor shaft is connected to a drive bellows mechanism, which will be discussed in detail in conjunction with FIGS. 2 and 3. The drive bellows mechanism is contained within a drive bellows housing 18. A transducer shaft extends from the end of the drive bellows remote from the motor and into a cone assembly 22, which contains the ultrasonic transducers of the probe. The transducers are located in a bath of ultrasonic fluid, which is injected into the probe through a fill port capped by a fill port plug 20. A slide pad 24 on the cone assembly 22 is moved during fluid filling to open a port on the cone assembly so that air bubbles can be expressed from the probe.

Figure 2:
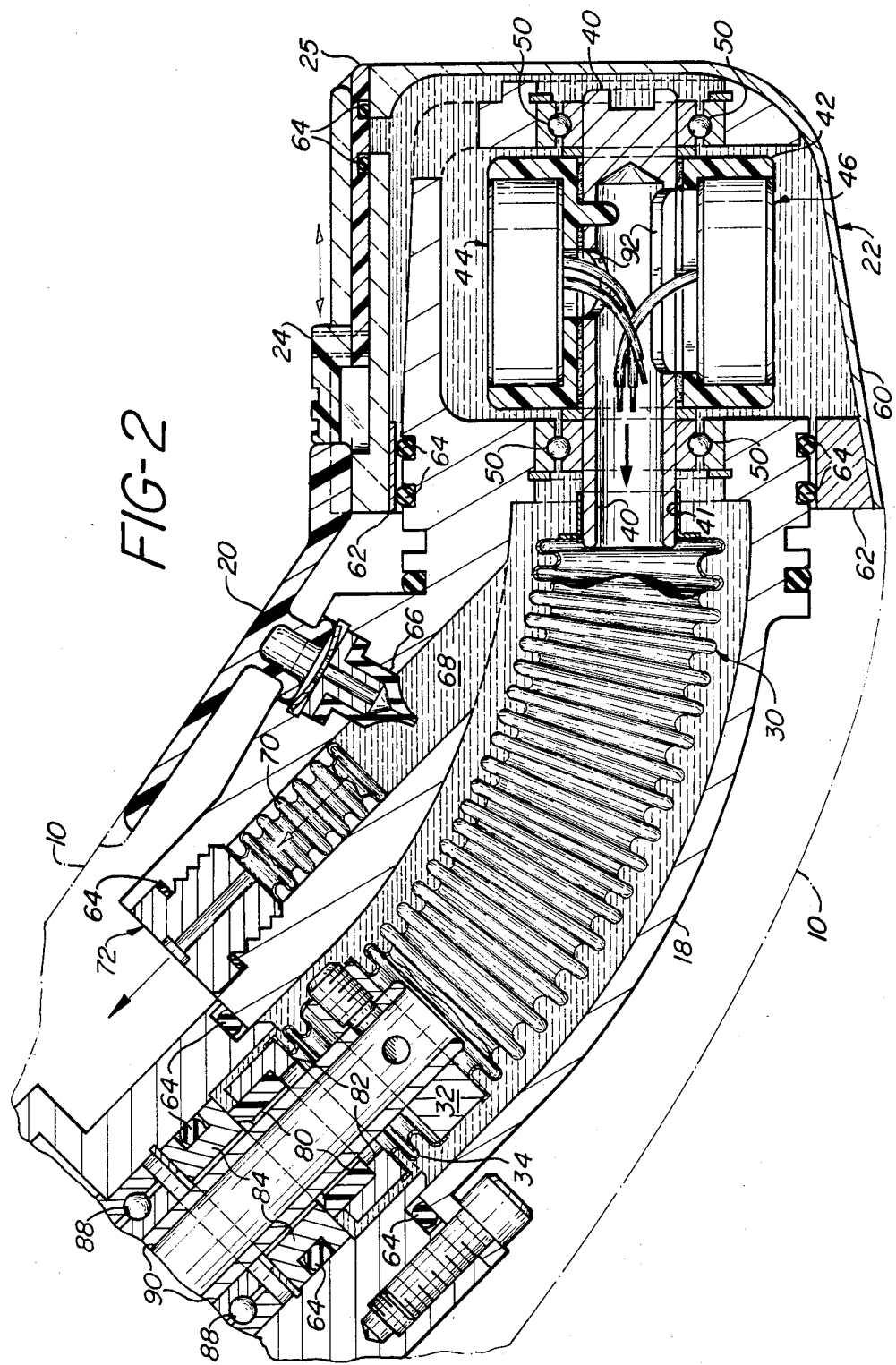
FIG. 2 illustrates a cross-sectional view of the transducer end portion of the ultrasonic transducer probe taken along a line 2—2 of FIG. 1.

Referring to FIG. 2, the transducer end of the probe of FIG. 1 is shown in cross-sectional detail. The drive bellows 30 is shown located in its housing 18 and surrounded by ultrasonic fluid within the housing. The lower right-hand end of the bellows in the FIGURE is soldered to the hollow transducer shaft 40, as shown by the solder joint 41. The transducer shaft 40 rides in transducer shaft bearings 50. Affixed to the shaft 40 between the bearings 50 is a transducer mount 42, upon which an imaging transducer 46 and a Doppler transducer 44 are located. In FIG. 2, the probe is shown in the imaging position with the imaging transducer 46 directed downward toward the acoustic window of the probe. The acoustic window is that portion of the cone assembly 22 through which ultrasonic energy passes to and from a transducer. For sector scanning the motor and bellows moves the transducer shaft and transducers back and forth in an oscillatory fashion. For Doppler measurement of fluid flow in the patient's body, the transducer shaft is rotated by approximately 180 degrees depending upon the vector angle to the point of flow measurement, and maintained in position so as to direct the Doppler transducer along a predetermined path out the acoustic window.

The wires which pass signals to and from the transducers run through the center of the apparatus. From the back of the transducers these wires pass through holes 92 in the transducer mount and transducer shaft 40, and then through the hollow shafts 40 and 90 and the hollow drive bellows 30. The wires exit the motor and encoder shaft 90 at the rear of the encoder, where they then continue as part of the cable 26. By running the wires through the center of the assembly, occurrences of wire breakage are minimized.

The fluid-filled cone assembly is contained by a transparent plastic cone 60. A metallic cone band 62 of varying thickness wraps around the inner edge of the cone and seals the fluid chamber by contact with O-ring seals 64 on the drive bellows housing 18.

Fluid is injected into the cone assembly by inserting a pressurizing syringe into a duckbill check valve 66 after removal of a fill port plug 20 for the valve. The injected fluid enters the assembly by way of a fill port 68. During fluid fill, a slide plate 25, which normally seals a hole in the cone 60, is retracted to open the hole by pushing back on a slide pad 24. Air bubbles which float to the top of the cone assembly chamber will then be forced out of the chamber during filling. Once the probe is pressurized with ultrasonic fluid after closure of the cone hole, the fluid pressure within the probe is maintained by a fill port compression bellows 70 and compression bellows plug 72. Should a leak occur in the probe, the bellows 70, which is under compression after fluid filling, will expand in the fill port 68 to maintain the proper fluid pressure in the probe.

At the rear of the drive bellows 30 toward the motor, the drive bellows is soldered to a bellows hub 32. The bellows hub is fastened to the motor and encoder shaft 90 by setscrews in the side of the hub. At the rear of the bellows hub 32 is a short seal bellows 34, which maintains the integrity of a face seal that seals the fluid chamber around the motor shaft 90. The seal bellows 34 is under compression and is soldered to a face seal mount 82. Secured to the face seal mount 82 is a dynamic face seal 80, which rotates against a static face seal 84 as the motor and encoder shaft 90 is rotated. The interface between the static and dynamic face seals 84 and 80 is always under compression to form a fluid seal as the motor and encoder shaft turns in its bearings 88.

Various O-ring seals 64 are shown throughout the FIGURE.

By sealing the fluid chamber around the motor and encoder shaft 90 and allowing the drive bellows to run in fluid, stress on the drive bellows is decreased, which permits a longer operating life for the system. The cone assembly fluid chamber could have been sealed around the transducer shaft in the vicinity of the rear transducer shaft bearings. Hovever, a seal at this point would require the torque of the bellows to overcome not only the inertial weight of the transducers and transducer mount, but also the resistance of the dynamic face seal around the transducer shaft. By locating the dynamic face seal around the motor and encoder shaft, the additional torque load on the drive bellows is removed, thereby prolonging the life of the drive bellows.

Figure 3:
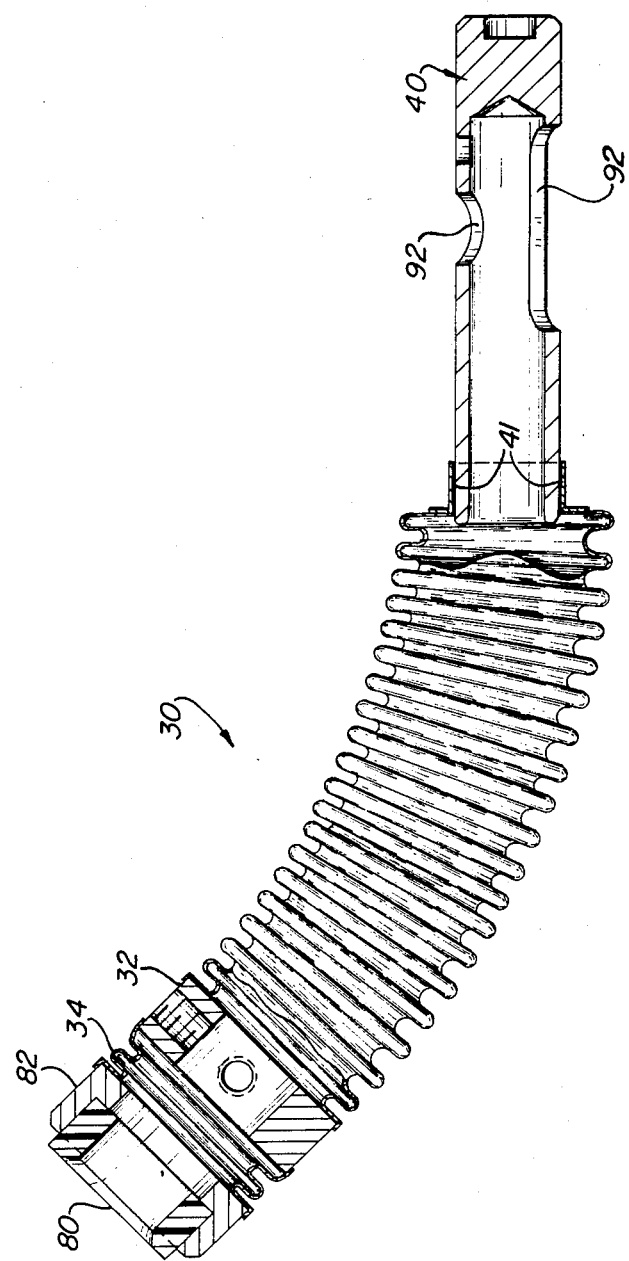
FIG. 3 illustrates the bellows drive mechanism of the ultrasonic transducer probe of FIGS. 1 and 2.

The bellows arrangement of FIG. 2 is shown in separate detail in FIG. 3. The bellows are made of nickel plated copper. The drive bellows 30 is about one and one-half inches long and one-half inch in diameter, and comprises about 39 convolutions. In operation, the drive bellows traverses an angle of 45 degrees and has a life expectancy of about $100 \times 10^6$ oscillations. One end of the drive bellows is soldered around the transducer shaft 40, and the other end is soldered around the bellows hub 32. The seal bellows 34 is about one-third of an inch in length and comprises about ten convolutions. It is soldered to the bellows hub 32 at one end, and to the face seal mount 82 at the other end.

Various other devices were considered for the drive mechanism of the ultrasonic transducer probe of the present invention, such as belts, gear drives, differentials, and U-joints. All were discarded in favor of the preferred bellows drive. As compared with belts, gear drives, and differentials, the bellows drive was found to have no backlash or angular misalignment. This results in greater accuracy of the correspondence of the positional information of the shaft encoder to the actual transducer position. As compared to a U-joint configuration, the bellows drive was found to provide a 1:1 correspondence in turns relationship between the motor shaft and the transducer shaft. In the case of a sector scanner this is especially important, since backlash at the points of turn-around during oscillation can result in an inaccurate image display. In the transducer probe of the present invention, a 1:1 turns relationship correspondence is needed over rotational span of 270° of transducer shaft movement, since the Doppler and imaging transducers are located on opposite sides of the shaft for mechanical balance. Without this kind of rotational accuracy, the Doppler signal could easily miss its intended intersection with a small vessel in the body while the display is indicating vessel intersection to the user.

The transducer probe assembly of FIG. 1 is easy to use and manipulate. The user grasps the case 10 around the area of the motor 12. Since the motor is the heaviest component of the probe, holding the probe in this manner allows it to be easily maneuvered since it is being held at approximately the balance point of the instrument. When so held, the cable 26 passes over the arm of the user and out of the way of the examination. The curved design of the probe also isolates the fluid-filled cone assembly 22 and drive bellows housing 18 from the electronics of the motor 12 and the encoder 16. In the upright position the motor and encoder are always above the fluid-filled components and away from any fluid leakage.

What is claimed is:

1. An ultrasonic transducer probe containing a moveable ultrasonic transducer, comprising:
    a motor having a first shaft;
    an ultrasonic transducer mounted on a second shaft; and
    a flexible cylindrical-shaped drive coupling connecting said first and second shafts and continuously bending in an arc delineated by the longitudinal axis of said cylindrical shape over substantially its entire length when said first and second shafts are oriented toward each other at an oblique angle;
    wherein said flexible coupling comprises a hollow bellows;
    wherein said ultrasonic transducer and said second shaft are located in a fluid-filled chamber; and
    further comprising a bellows housing surrounding said bellows and connected to said motor and said fluid-filled chamber,
    wherein said bellows housing is fluid-filled, and further comprising a dynamic fluid seal surrounding said first shaft.

2. The ultrasonic transducer probe of claim 1, further comprising:
    a fill port for filling said fluid-filled chamber; and
    a closeable aperture connected to said fluid-filled chamber, and suitable for being opened during filling to express excess fluid and air bubbles from said chamber.

3. An ultrasonic transducer probe comprising:
    a motor having a first shaft;
    an ultrasonic transducer mounted on a second shaft;
    a flexible coupling connecting said first and second shafts;
    wherein said ultrasonic transducer, said first shaft and said flexible coupling are surrounded by a fluid chamber; and
    a dynamic fluid seal located around said first shaft.

4. The ultrasonic transducer probe of claim 3, wherein said dynamic fluid seal is a face seal, and further comprising means connected to said face seal for maintaining the integrity of said face seal.

5. The ultrasonic transducer probe of claim 4, wherein said means for maintaining comprises a compression bellows located around said first shaft for urging said dynamic seal in a fluid-tight condition.

* * * * *